(12) United States Patent
Van Bree et al.

(10) Patent No.: US 9,694,193 B2
(45) Date of Patent: Jul. 4, 2017

(54) DEVICE AND METHOD FOR TREATING CELLS

(75) Inventors: Johannes Wilhelmus Maria Van Bree, Eindhoven (NL); August Johannes Marie Pemen, Breda (NL); Eva Stoffels, Retie (BE)

(73) Assignee: TECHNISCHE UNIVERSITEIT EINDHOVEN, Eindhoven (NL)

( * ) Notice: Subject to any disclaimer, the term of this patent is extended or adjusted under 35 U.S.C. 154(b) by 0 days.

(21) Appl. No.: 13/202,876

(22) PCT Filed: Mar. 3, 2010

(86) PCT No.: PCT/NL2010/050106
§ 371 (c)(1),
(2), (4) Date: Nov. 1, 2011

(87) PCT Pub. No.: WO2010/101461
PCT Pub. Date: Sep. 10, 2010

(65) Prior Publication Data
US 2012/0064594 A1 Mar. 15, 2012

Related U.S. Application Data
(60) Provisional application No. 61/156,986, filed on Mar. 3, 2009.

(30) Foreign Application Priority Data

Mar. 3, 2009 (EP) ...................................... 09154239
Dec. 15, 2009 (NL) ...................................... 2003958

(51) Int. Cl.
*A61N 1/40* (2006.01)
*C12M 1/42* (2006.01)
(Continued)

(52) U.S. Cl.
CPC ................ *A61N 1/40* (2013.01); *C12M 35/02* (2013.01); *C12N 13/00* (2013.01); *C12M 23/12* (2013.01); *C12N 15/87* (2013.01)

(58) Field of Classification Search
CPC ......... A61N 1/40; C12M 23/12; C12M 35/02; C12N 13/00; C12N 15/87; H03K 3/57
(Continued)

(56) References Cited

U.S. PATENT DOCUMENTS 4,280,098 A * 7/1981 Veraldi ......................... 327/365
4,906,576 A * 3/1990 Marshall, III ............. 435/285.2
(Continued)

FOREIGN PATENT DOCUMENTS

DE 21 16 869 10/1971
WO 85/02094 5/1985
(Continued)

OTHER PUBLICATIONS

Allen, et al, "The Electric Field in Single-Turn and Multi-Sector Coils," Il Nuovo Cimento, vol. XXI, N. 6, pp. 980-987 (1961).
(Continued)

*Primary Examiner* — Michael Hobbs
(74) *Attorney, Agent, or Firm* — Nixon & Vanderhye P.C.

(57) ABSTRACT

The present invention relates to a device for treating biological cells in an object, the device comprising: —a single winding coil element; —an electrical generator connected to the single winding coil element, the single winding being configured to be positioned essentially around the object; wherein the electrical generator is configured to discharge into the single winding coil element so that the single winding coil element generates a short duration pulsed electromagnetic field by magnetic induction in the single winding coil element, the electromagnetic field having a field strength that is sufficiently high to affect, preferably
(Continued)

increase the permeability of cell membranes and/or intracellular membranes of the biological cells contained in the object when in operation the object is placed inside the single winding coil element.

19 Claims, 4 Drawing Sheets

(51) Int. Cl.
  *C12N 13/00* (2006.01)
  *C12N 15/87* (2006.01)
  *C12M 1/32* (2006.01)

(58) Field of Classification Search
  USPC .............. 435/273.6, 283.1; 426/237; 99/451
  See application file for complete search history.

(56) References Cited

U.S. PATENT DOCUMENTS

| | | | |
|---|---|---|---|
| 5,132,419 A * | 7/1992 | Lanz et al. ..................... | 540/215 |
| 5,798,579 A * | 8/1998 | McPhee ................. | H03K 3/537 |
| | | | 307/106 |
| 2002/0147424 A1 | 10/2002 | Ostrow | |
| 2007/0051685 A1* | 3/2007 | Wittmer et al. .............. | 210/695 |
| 2009/0125091 A1* | 5/2009 | Schoenbach et al. ........ | 607/156 |

FOREIGN PATENT DOCUMENTS

| WO | WO 03/104385 | 12/2003 |
|---|---|---|
| WO | 2005/071057 | 8/2005 |
| WO | WO 2007/072472 | 6/2007 |
| WO | WO 2008/100749 | 8/2008 |

OTHER PUBLICATIONS

International Search Report for PCT/EP2009/067258, mailed May 11, 2010.
Mori, Y. et al., "Magnetic Field Design of a Superconducting Magnet for a FFAG Accelerator", IEEE Transactions on Applied Superconductivity, vol. 15, No. 2, (Jun. 1, 2005), pp. 1185-1188.
Olofsson, J. et al., "Single-cell electroporation", Current Opinion in Biotechnology, vol. 14, No. 1, (Feb. 1, 2003), pp. 29-34.
Favard, C. et al., "Electrotransfer as a non viral method of gene delivery", Current Gene Therapy, vol. 7, No. 1, (Feb. 1, 2007), pp. 67-77.
Obana et al., "Magnetic Field Design of a Superconducting Magnet for a FFAG Accelerator", IEEE Transactions on Applied Superconductivity, vol. 15, No. 2, (Jun. 1, 2005), pp. 1185-1188.
Obana et al, *Magnetic Field Design of a Superconducting Magnet for a FFAG Accelerator*, IEEE Transactions on Applied Superconductivity, vol. 15, No. 2, Jun. 2005.
Schoenbach et al; *The Effect of Pulsed Electric Fields on Biological Cells: Experiments and Applications*, IEEE Transactions on Plasma Science, vol. 25, No. 2, Apr. 1997.
Shi et al; *Generation and Measurement on High Pulsed Magnetic Filed of µs Level*, High Voltage Apparatus, vol. 37, No. 2, Apr. 24, 2011 (Article ID: 1001-1609(2001)02-0024-02).
CN Office Action, Appln. No. 201080010675.4 (May 17, 2013).
Stoffels et al., "*Effects of the Electrical Field on the 3T3 cells*", IFMBE Proceedings 13th International Conference on Biomedical Engineering, vol. 23, pp. 1389-1392 (Dec. 3-6, 2008).
Torricelli et al., "Biomimetic PMMA-based bone substitutes: A comparative in vitro evaluation of the effects of pulsed electromagnetic field exposure," Journal of Biomedical Materials Research Part A, vol. 64A, Issue 1, pp. 182-188, Jan. 1, 2003 (Abstract).

* cited by examiner

DEVICE AND METHOD FOR TREATING CELLS

This application is the U.S. national phase of International Application No. PCT/NL2010/050106, filed 3 Mar. 2010, which designated the U.S. and claims priority to EP Application No. 09154239.9, filed 3 Mar. 2009; and NL Application No. 2003958, filed 15 Dec. 2009; and claims the benefit of U.S. Provisional Application No. 61/156,986, filed 3 Mar. 2009, the entire contents of each of which are hereby incorporated by reference.

FIELD

The present invention relates to device and method for treating biological cells in an object.

BACKGROUND AND SUMMARY

Pulsed electromagnetic field processing is a way of affecting biological cells by means of brief pulses of a strong external electromagnetic field. In pulsed electromagnetic field processing two electrodes are placed in a medium comprising biological cells. Then the pulsed electromagnetic field is applied to the medium. The applied electromagnetic field may affect the membranes and/or the intracellular structures of the cells, depending on the field strength and pulse shape (including the time duration and steepness of the pulse). More specifically, a process known as electroporation may occur, which means that the permeability of the cell membrane and/or of the intracellular membrane increases as a result of the electromagnetic field applied to the medium.

When electroporation occurs at the cell membrane, protein channels in the cell membrane may open, causing a change in ion concentration. This change in ion concentration may result in cell stress. When the applied electromagnetic field strength is such that the voltage over the cell membrane is about a critical threshold, for instance a threshold of 1 Volt, and of relative short duration, the cell will recover itself. This effect may be used, for instance, to locally deliver material (such as genes or drugs) into the cells. Applying higher electromagnetic field strengths causing a higher voltage across the cell membrane, and/or applying field pulses of a longer duration, may result in irreversible damage to the cell instead and may eventually even lead to cell death. This effect may be used for processing food, for instance for the cold-pasteurization of fruit juices, or for inducing apoptosis, i.e. programmed cell death in the treatment of diseases such as cancer.

The critical threshold for affecting the cell membrane of the biological cells in the medium may vary, but typically amounts to about 1 Volt. If the typical size of the cells is about 10 μm, the externally applied electric field strength should be in the order of magnitude of 1 kV/cm. This is a very high field strength and in practice it has been difficult to generate electric fields of sufficient strength in the biological cells to be treated.

Furthermore, since electrodes are to be placed inside the medium to be able to generate therein the pulsed electromagnetic field, the biological cells of the medium should be treated first while being in contact with the electrodes, and can be placed in an object, i.e. can be packed into a container, carton, pack(age), etc., only after the cell treatment has been completed. This may reduce the efficiency of the treatment operation considerably.

Another drawback of using electrodes for generating the pulsed electromagnetic field is that the electrodes may erode over time, meaning that eroded electrode material eventually may end up in the medium to be treated. Also electrochemical reactions may occur at or around the electrodes. Such reactions may result in unwanted reaction residues. If the medium includes foodstuff to be consumed by human beings, this may involve an unacceptable health risk.

It is an object of the present invention to provide a method and device for treating biological cells in an object wherein at least one of the above-identified and/or other drawbacks of the prior art have been removed or at least reduced.

It is a more specific object of embodiments of the invention to provide a method and device wherein biological cells in an object may be treated in a fast and efficient manner.

It is a more specific object of embodiments of the invention to provide a method and device wherein biological cells present inside an object may be treated without the need to place one or more electrodes in the object.

According to a first aspect of the invention a device for treating biological cells in an object, the device comprising:
 a single winding coil element;
 an electrical generator connected to the single winding coil element, the single winding being configured to be positioned essentially around the object;
 wherein the electrical generator is configured to discharge into the single winding coil element so that the single winding coil element generates a short duration pulsed electromagnetic field by magnetic induction in the single winding coil element, the electromagnetic field having a field strength that is sufficiently high to affect, preferably increase the permeability of, cell membranes and/or intracellular membranes of the biological cells contained in the object when in operation the object is placed inside the single winding coil element. The device may be electrodeless and therefore the disadvantages associated by the use of electrodes are not present. Furthermore, by placing the object inside the single winding of the coil element the biological cells in the object may be treated without the presence of any electrical element, such as an electrode, in the object. Contact between the device that generated the electromagnetic field and the biological cells can therefore be avoided. Furthermore, since the electromagnetic field is induced by means of a short duration magnetic field, an electric field with the required field strength of at least 1 kV/cm (for affecting cell membranes) or at least 10 kV/cm (for affecting the intracellular membranes) can be realized within a relatively short period of time. Any electroporation brought about in the cells may be used for different purposes, for instance for introducing drugs into the cells. In order to generate the short duration high strength electromagnetic fields needed to bring about the desired effect on the cell membranes and/or the intracellular membranes, a single winding coil element is used. Using a single winding coil element and/or a coaxially built circuit the self-inductance of the coil element and circuit can be kept relatively low, which means that a short rise time of the current in the coil element may be realised. A self-inductance of several tens of nanoHenrys or less can be achieved easily in this embodiment.

In an embodiment the electromagnetic field is applied electrodelessly to the biological cells in the object. Contamination risks due to erosion of the electrodes which in the case of foodstuffs may lead to unacceptable health risks are eliminated.

In a further embodiment the single winding coil element has a generally circular or oval shape in cross-section. This shape allows to generate a pattern of the electromagnetic field that is suitable for affecting, preferably increasing the permeability, of cell membranes and/or intracellular membranes of the biological cells.

In an embodiment the single winding coil element is essentially cylindrical and defines a receiving space sized to allow the object comprising the biological cells to be removably placed. The electromagnetic field is applied when the coil element is placed around the object containing the biological cells or the object is placed inside the receiving space of the single winding coil element. The cylindrical shape of the single winding enables that the entire content in the object is subjected to the high electromagnetic field generated by the single winding coil element.

In an embodiment the single winding coil element defines a receiving space sized to allow the object to pass through the single winding. The object comprising the biological cells can be moved through a stationary single winding of the coil element thereby being subjected to the electromagnetic field. In a further embodiment the coil element can be moved in such a way that the single winding moves along one or more stationary objects comprising biological cells that pass through the receiving space defined by the single winding coil element. In even a further embodiment the coil element comprises multiple single windings, for example arranged in a one-, two-, or three-dimensional array. Again, one or more objects can be passed through the receiving spaces of the respective single windings and/or the single windings can be moved along the one or more objects.

In an embodiment the single winding coil element is configured to allow placement of the object concentrically in the coil element. This may allow the biological cells contained in the object to be subjected to a relatively uniform electromagnetic field of sufficient field strength to affect the cell membranes and/or the intracellular membranes.

In an embodiment the single winding coil is configured to affect the biological cells within the object without contact between the cells and the single winding coil. The absence of physical contact between the single winding coil and the cells to be treated avoids the abovementioned drawbacks of devices employing electrodes for generating and applying the electromagnetic field.

In an embodiment the electrical generator comprises a capacitor arranged so as to generate an electric field strength inside the single winding coil element of at least 10 kV/cm. At least this value of the electric field strength is required to affect the intracellular membranes of the cells.

In an embodiment the winding of the single winding coil element comprises two terminals defining a gap in between. The width of the gap largely determines the pattern of the electromagnetic field and its ability to affect the cell membranes and/or the intracellular membranes of the biological cells in the object that is placed inside the receiving space defined by the single winding coil.

In an embodiment the electrical generator comprises a power supply, a capacitor and a switching element, the switching element being configured for charging the capacitor in a first stage and discharging the capacitor in a second stage so as to provide a short duration high current in the single winding coil element.

In an embodiment the switching element comprises a multiple-gap spark gap switch, preferably a two-gap spark gap switch, configured to break down at a predefined discharge voltage.

In an embodiment the current rise time is 10 ns or less, preferably 6 ns or less, the rate of change of the current (dI/dt) is at least 100 A/ns, preferably at least 150 A/ns, the amplitude of the current pulse is about 500-2000 A, and/or the self-inductance of a circuit comprising the single winding coil element is several tens of nanoHenrys The switching element may be formed by a multiple-gap spark gap switch, preferably a two-gap spark gap switch, configured to break down at a predefined discharge voltage. The circuit may be built coaxially so that the self inductance is kept to a minimum. These embodiments make it possible to realize a relatively short time duration of the electromagnetic field. More specifically, the rise time of the current in the single winding coil element can be 10 ns or less, preferably 6 ns or less. Moreover, the rate of change of the current (dI/dt) is at least 100 A/ns, preferably at least 150 A/ns, resulting in an amplitude of the current pulse in the single winding coil element of about 500-2000 A. In embodiments of the invention the total duration of the pulse is about several hundreds of nanoseconds, preferably 300 ns.

In an embodiment the generator is at least partly arranged in an enclosure and is pressurized to a predetermined high pressure value, preferably a pressure of at least about 8 bar. The circuit is built coaxially and kept as small as possible to keep the self inductance low of the circuit. In order to reduce the size of the device, more specifically the mutual distance between the elements (for example the multiple spark gap switch), the generator may at least partly be arranged in an enclosure. The enclosure is then pressurized to a predetermined high pressure value, for instance at least about 8 bar.

According to a further aspect an assembly of the device and an object comprising biological cells is provided, the object being arranged in the single winding coil element. The object may be tissue or any solid containing the biological cells. In other embodiments the object is a holder for holding a medium including said biological cells, for instance foodstuffs.

According to another aspect of the invention a method of treating biological cells in an object is provided, the method comprising:
 positioning the object inside a single winding of a single winding coil element connected to an electrical generator;
 discharging the electrical generator into the single winding coil element so as to generate a short duration pulsed electromagnetic field by magnetic induction in the single winding coil element, wherein the electromagnetic field strength is sufficiently high to affect cell membranes and/or intracellular membranes of the biological cells contained in the object, preferably sufficiently high to increase the permeability of the cell membranes and/or intracellular membranes.

Preferably the method is suitable for increasing the cell growth rate of the biological cells, and/or increasing the metabolic activity of the biological cells. Advantageously, the biological cells can remain in the medium in which they are contained. There is no need to transfer them to another medium suitable for conventional electroporation.

In an embodiment the method comprises generating an electric field in the object that is sufficiently high, preferably with an electric field strength inside the single winding coil element of at least 1 kV/cm, to affect, preferably increase the permeability of cell membranes and/or intracellular membranes of, the biological cells contained in the object.

In an embodiment the method comprises in a first stage charging a capacitor and in a second stage discharging the capacitor in a second stage so as to provide a short duration high current in the single winding coil element.

In a further embodiment the method comprises increasing the cell growth rate of the biological cells, and/or increasing the metabolic activity of the biological cells.

According to another aspect of the invention a method is provided comprising applying a pulsed electromagnetic field to the biological cells, the electromagnetic field having a field strength sufficiently high to affect, preferably increase the permeability of, cell membranes and/or intracellular membranes of the biological cells contained in the object, wherein the time duration of applying the field to the cells is kept between a minimum treatment time and a maximum treatment time, the treatment time being selected to increase the cell growth rate of the biological cells. The pulsed electromagnetic field may be applied using one or more of the earlier mentioned single winding coils. However, the method also encompasses embodiments wherein the electromagnetic field is applied in a different way, for instance—but not limited to this—by using electrodes, parallel plates, antennas or similar electromagnetic field generating devices.

BRIEF DESCRIPTION OF THE DRAWINGS

Further advantages, characteristics and details of the present invention will become apparent from the following description of preferred embodiments thereof. In the description reference is made to the annexed drawings.

DETAILED DESCRIPTION

Exposing biological cells to pulsed electromagnetic fields is used in many applications. Common practice is to use two or more electrodes comprising conductive material that are arranged opposite of each other for creating an electromagnetic field. Examples of the use of electrodes to expose biological cells to pulsed electromagnetic fields can, among others, be found in equipment for pasteurization (PEF), transfection and micro clamping, apoptosis induction (nsPEF, sm/i-PEF, HISDEP, UPSET).

In general, the biological cells are exposed to brief pulses of a strong external electromagnetic field. This strong electromagnetic field is generated by two or more electrodes that are placed in a medium comprising the biological cells. Then the pulsed electromagnetic field is applied to the medium. The applied electromagnetic field may affect the cell membranes and/or the intracellular membranes and/or structures of the biological cells, depending on the field strength and pulse shape (including the time duration and steepness of the pulse) and may cause a reversible of irreversible effect. In the context of this invention the terms intercellular and intracellular may be used interchangeably. Applying low electromagnetic field strengths across the cell membrane, several volts per centimeter, for instance 20V/cm, may cause voltage-dependent channels in the cell membrane to open, causing a change in ion concentration. This change in ion concentration may result in cell stress. Applying high electromagnetic field strengths across the cell membrane, several kilovolts per centimeter, for instance 1 kV/cm, may cause the permeability of the cell membrane to increase. The cell needs seconds to hours to recover (reversible breakdown) from this increase of permeability or cell death (irreversible breakdown) may occur. A treatment comprising the application of external electromagnetic fields may cause a temporarily increase of permeability of the cell membrane, which may be used for transfection and microclamping. Such treatment can also cause permanent irreversible effects, which may be used for processing food, for instance for cold-pasteurization.

The use of electrodes has several drawbacks:

it is an invasive technique as the electrodes need to be in direct contact with the medium containing the biological cells;

it comprises contamination risks; and it requires additional steps before and/or after treatment of the biological cells in the object for example to at least reduce the chance of an electrical breakdown.

Since electrodes are to be placed inside the medium to be able to generate therein the pulsed electromagnetic field, the biological cells of the medium should be treated first while being in contact with the electrodes, and can be placed in an object, i.e. can be packed into a container, carton, pack(age), etc., only after the cell treatment has been completed. This may reduce the efficiency of the treatment operation considerably.

A well known drawback of using electrodes for generating the pulsed electromagnetic field is that the electrodes may erode over time, meaning that eroded electrode material eventually may end up in the medium to be treated. Also electrochemical reactions may occur at or around the electrodes. Such reactions may result in undesired reaction residues. If the medium includes foodstuff to be consumed by for example human beings, this contamination risk may involve an unacceptable health risk.

Coating or shielding the electrodes to at least reduce the abovementioned drawbacks is often not an option, since the coating or shielding will fade out the electromagnetic field across the medium containing for example the biological cells to be treated. To reduce the effects of corrosion sometimes noble metals are used. However this does not reduce the other drawbacks.

Furthermore, the use of electrodes often requires additional steps, such as temporarily replacing the cells in a special environment containing the electrodes (e.g. an electroporation cuvette). Another example of an additional step needed is the washing of cells and putting them in salt-free medium to at least reduce the chance of an electrical breakdown. After treatment the cells usually have to be put back in their initial environment and/or medium.

Biological cells can be divided into two types, eukaryotes and prokaryotes. An important difference between the two cell types is that prokaryote cells are lacking a cell nucleus and organelles. This means that the DNA is floating freely within the cell. Both cell types are enclosed by a membrane, contain DNA (which contain instructions to make for example ribosomes and RNA), cytoplasm and ribosomes. Ribosomes build proteins according to the templates held within the messenger RNA. Bacteria and Archaea are of the type prokaryotes. The size of prokaryotes is generally between 0.5 µm and 2 µm. Animals, plants and fungi are of the type eukaryotes. These cells have a nucleus, a membrane enclosed organelle which hold genetic material, and other organelles which are also bound by a membrane. Two important organelles are the endoplasmic reticulum and the mitochondrion. The endoplasmic reticulum provides transport in the cell and therefore can for example detoxify poison in a liver. The mitochondrion is in fact a bacteria (prokaryote) living inside an eukaryote and contains it own DNA to replicate itself. It's function is to breakdown nutrients and thereby generating energy. The cell size of eukaryotes is generally between 2 µm and 10 µm.

The cell membrane plays a major role in electroporation and is explained in some more detail. As mentioned before, all cells are enclosed by a membrane. The membrane protects the interior of the cell and regulates the passage of materials. The main structure of the membrane is a bilayer of lipids. Lipid soluble substances, oxygen and carbon dioxide, are able to flow through this layer. The membrane also comprises other proteins that help water soluble substances, glucose and amino acids, to pass. Some of these protein channels open or close when there is a change in voltage across the cell membrane. These channels are called voltage-gated ion channels. So when an externally electric field is applied, these protein channels open up and cause a change in the ion concentration.

For eukaryotes the organelles are also bounded by a membrane (intracellular membrane). The intracellular membranes may also be affected by an externally applied electromagnetic field.

As mentioned earlier, in the electroporation process the permeability of the membrane increases. Electroporation occurs when an external electromagnetic field is applied to the biological cell. Depending on for instance the charging time of the membrane electroporation occurs at either the cell membrane or the intracellular membrane. When the electromagnetic field is not too high (so that the voltage across the membrane is about a critical threshold of 1 Volt) and of relative short duration, the cell will recover itself. Electroporation can be applied for example in gene transport and drug delivery. The application of higher electromagnetic fields, higher voltages across the cell membrane, and/or a longer duration may cause irreversible damage to the cell and eventually cell death.

Typically a voltage of at least 1 Volt is needed to affect the cell membrane. Since the size of a eukaryote is around 10 µm, the external electric field should be in the order of magnitude of about 1 kV/cm over the cell membrane. The required membrane voltage to affect the cell's intracellular membrane is found to be of the same order of magnitude as the voltage needed to affect the cell membrane and therefore is about 1 V. However, the dimensions of the intracellular structures are roughly a factor 10 smaller compared to the cell size. This means that the electric field strength should be at least about 10 kV/cm.

Figure 1:
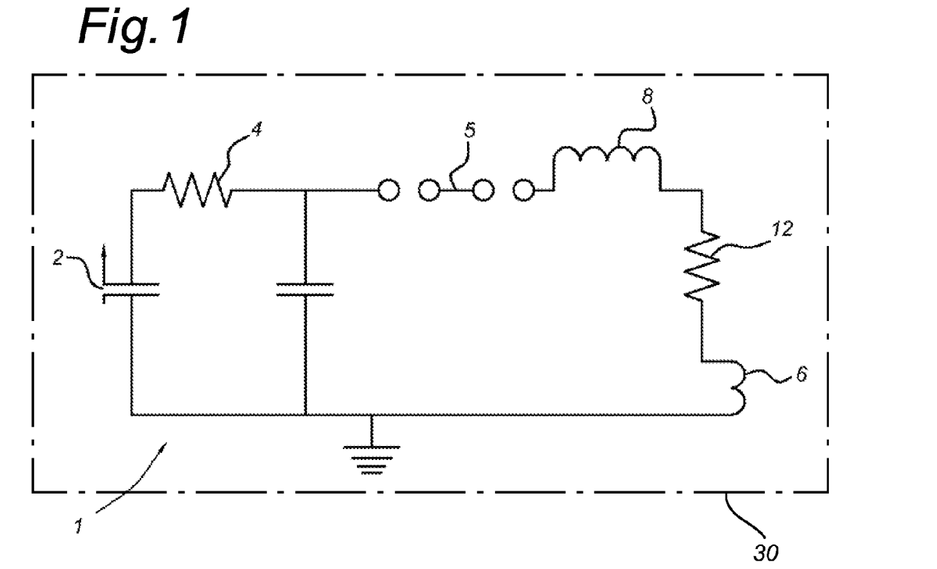
FIG. 1 shows the general layout of an embodiment of the present invention.

FIG. 1 shows a circuit diagram of an embodiment for generating the pulsed electromagnetic field needed to affect the biological cells of a medium present in an object, for instance milk in a milk carton. The circuit 1 comprises a power source 2 (for instance a voltage source), a resistor 4, a switching element 5 and a single winding coil 6 and optionally a damping resistor 12 in series. Parallel to the power source 2 a capacitor 3 is arranged. Furthermore an element 8 is shown that represents the self-inductance of the circuit 1. Resistor 12 can be optionally added to even increase the rise time of the current through the single winding coil.

In an embodiment the switching element is comprised of a multiple spark gap switch. A multiple spark gap switch generally comprises an arrangement of conducting electrodes separated by a plurality of gaps. When a suitable voltage supplied, sparks may be formed, causing ionization of the medium between the electrodes (for instance air) and reducing the electrical resistance of the switch. An electric current then flows until the path of ionized gas is broken or the current is reduced below a minimum current value.

Figure 2:
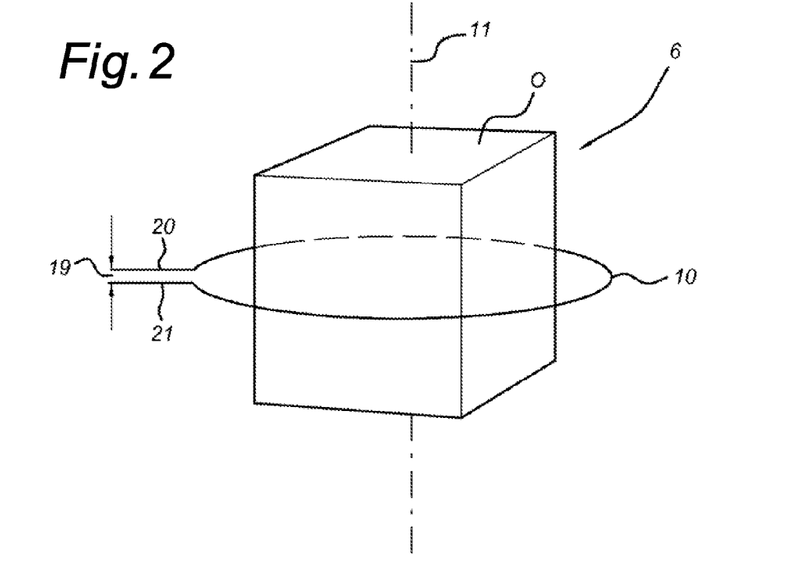
FIG. 2 shows a more detailed view of the embodiment of figure including an object placed in the interior of the single winding coil.
Figure 3:
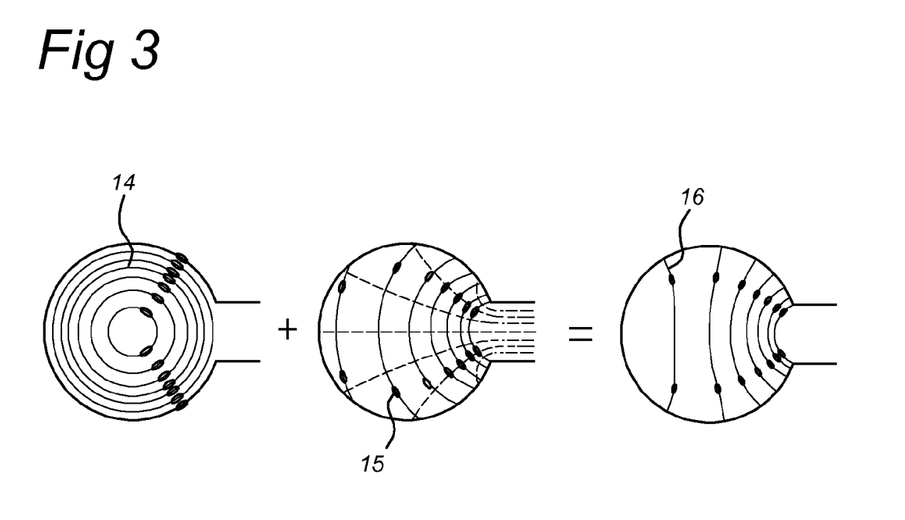
FIG. 3 are schematic representations of the electric field generated by the single winding coil of FIGS. 1 and 2.

Referring to FIG. 2, the single winding coil 6 comprises an essentially circular winding 10. Parallel to the axial direction 11 of the single winding coil 6, for instance concentrically with the winding, an object (O) containing biological cells to be treated is placed. It can be shown that the electric field generated by the single winding coil 6 of the present embodiment, as represented in FIG. 3 by field lines 16, may be considered a superposition of a rotational field (represented by field lines 14) and a conservative field (represented by field lines 15). From FIG. 4 follows that the electric field may be made especially strong close to the gap 19 of the single winding coil 6.

Figure 8:
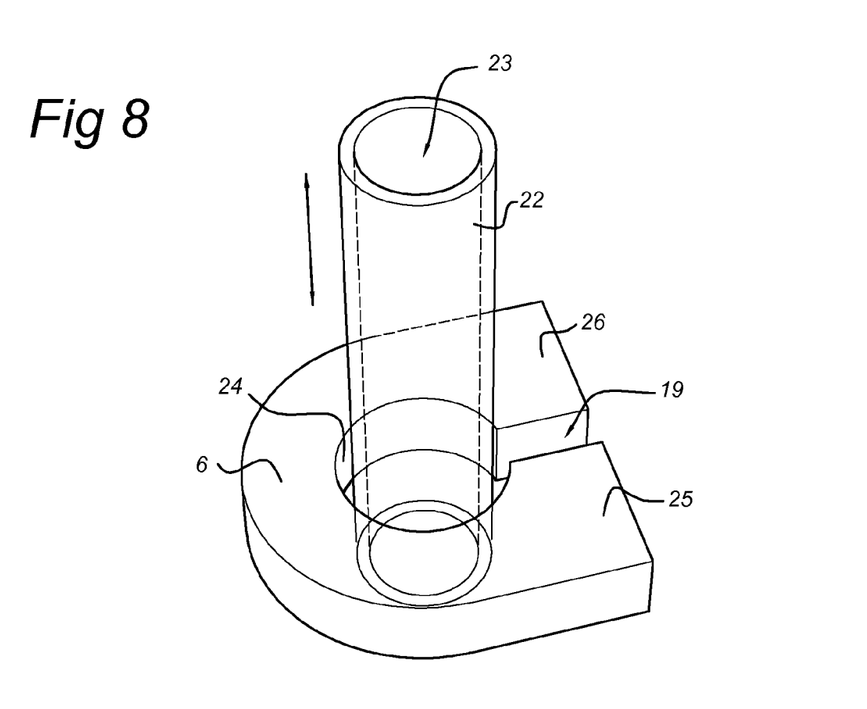
FIG. 8 is a schematical view in perspective of an embodiment of a single winding coil having a receiving space wherein a holder containing biological cells is arranged.

FIG. 8 shows an embodiment of the single winding coil 6 according to the invention. In this embodiment the single winding coil is essentially cylindrical, more specifically horseshoe-shaped. At one location the wall of the cylinder is interrupted by the gap 19. On either side of the gap 19 the coil element 6 comprises terminals 25,26 for attachment of the leads of the multiple spark gap switch.

The coil element defines a receiving space 24 in which an object, such as a holder or container 23, can be arranged, for instance by moving the holder or container downward into the space 24. After treating the biological cells the holder or container 22 containing the biological cells (or, more generally, the object) may be removed from the receiving space by moving the container or holder downward or upward. During the entire procedure there is no need to bring the container or holder into contact with the single winding coil 6.

In another embodiment the biological cells are arranged inside a tube, channel or similar passage extending through the receiving space. The biological cells transported along the passage. During transport they are subjected to the high electromagnetic field generated by the single winding coil 6. The transport of cells may be performed in a batch-like manner, but a continuous flow of cells along one or more consecutive single winding coils 6 is also conceivable.

In an embodiment the generator is at least partly arranged in an enclosure 30 (see FIG. 1) and is pressurized to a predetermined high pressure value, preferably a pressure of at least about 8 bar. The circuit 1 is built coaxially and kept as small as possible to keep the self inductance low of the circuit. In order to reduce the size of the device, more specifically the mutual distance between the elements (for example the multiple spark gap switch), the generator may at least partly be arranged in an enclosure 30. The enclosure 30 is then pressurized to a predetermined high pressure value, for instance at least about 8 bar.

In operation, the voltage source 2 charges the capacitor 3 causing a rise of the voltage until the spark gaps of the multiple spark gap switch 5 fire. The spark gap switch can be seen as a switch which closes by a specified voltage. This voltage is dependent on the mutual distances (gaps) of the electrodes and the pressure of medium between the electrodes. A greater distance and/or higher (air) pressure will cause a higher breakdown voltage. When the spark gap switch 5 fires, the capacitor 3 discharges into the single winding coil 6 generating therein a pulse-shaped current signal. The current in the single winding coil 6 generates a short and intense magnetic field, inducing a very strong electric field in the object (O).

The self-inductance (typically about 50-150 nH) of the circuit arrangement is relevant for the rise time of the current through the circuit (and therefore for the strength of the electric field created inside the object). The inductance of the single winding coil itself is considerably lower, for instance in the order of magnitude of 1-5 nH.

The rising current through the single winding coil 6 generates an electric field. The strength of the electric field largely depends on the rise time and the amplitude of the current through the single winding coil 6. In case the rise time of the current through the circuit is less than 10 ns, preferably 6 ns or less and the amplitude of the current through the circuit is more than 1000 A, the electric field strength in the object (O) may become larger than 10 kV/cm. This electric field is strong enough to affect the cells present in the object (O). If the object is a milk carton holding a certain amount of milk, the electric field applied may be sufficient to affect the cells in the milk in such a way, that a cold-pasteurization of the milk takes place.

A series of tests was performed to determine the effects of applying an electromagnetic field of the above specified current rise time to biological cells of an object. The test were performed on 3T3 cells originating from the primary mouse embryonic fibroblasts and cultured by the 3T3 protocol. 3T3 is an abbreviation of "3-day transfer, inoculum $3 \times 10^5$ cells". Fibroblasts are mammal cells, eukaryote type, and are an important part of connective tissue. They make structural fibres and ground substance of connective tissue and play a role in wound healing. The 3T3 cells were cultured and then transferred to well plates and after 2-3 days in culture the cells were counted and transferred to Eppendorf tubes to be tested. A so-called dose response test was performed wherein the effects of different treatment times were determined. The treatment times used were 1, 2, 3, 4, 5, 10 and 15 minutes, corresponding (in the specific measurement set up) to between about 400 and 6000 pulses. During these tests the pulse source operated at 7 pulses per second, with a peak current of about 1200 A and a rise time of about 6 ns. After treatment both the untreated and treated cells were put back into an incubator and checks were performed at regular times during this incubation.

The number of cells from the same sample was determined after a treatment time varying from 0 (i.e. no treatment at all) up to 15 minutes. The number of cells showed a decrease at a treatment time of 10 and 15 minutes, as expected. However, the test also showed that the number of cells at a treatment time of 2, 4 and 5 minutes surprisingly increased rather than decreased.

Clearly, the cells were affected by the pulsed electromagnetic field. A dose experiment was performed and the cells were counted every day after treatment by a NucleoCounter. A NucleoCounter is a system that detects fluorescent signals bound to a cell nuclei and as such is known to the skilled person. The results of this counting step are shown in FIGS. 4 and 5.

Figure 4:
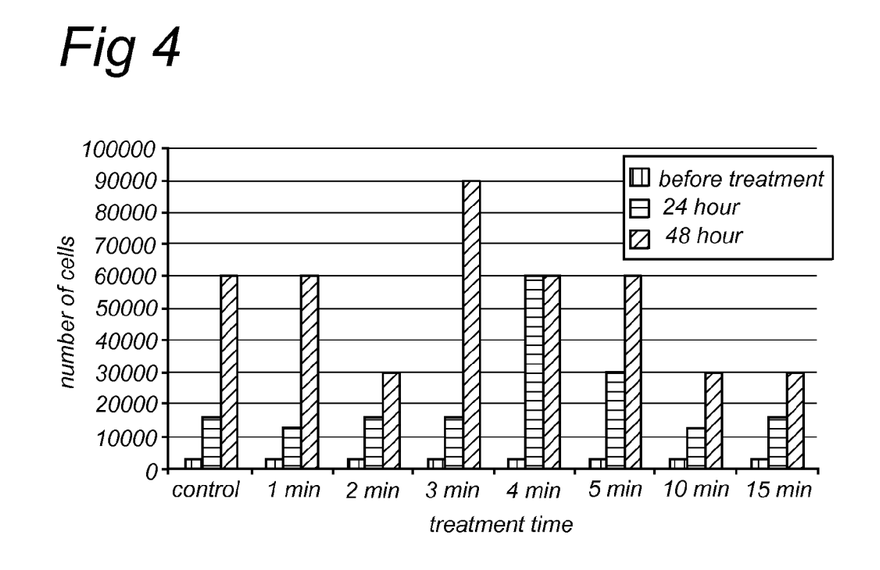
FIGS. 4 and 5 are graphical representations of the experiments performed using an embodiment of the present invention.
Figure 5:
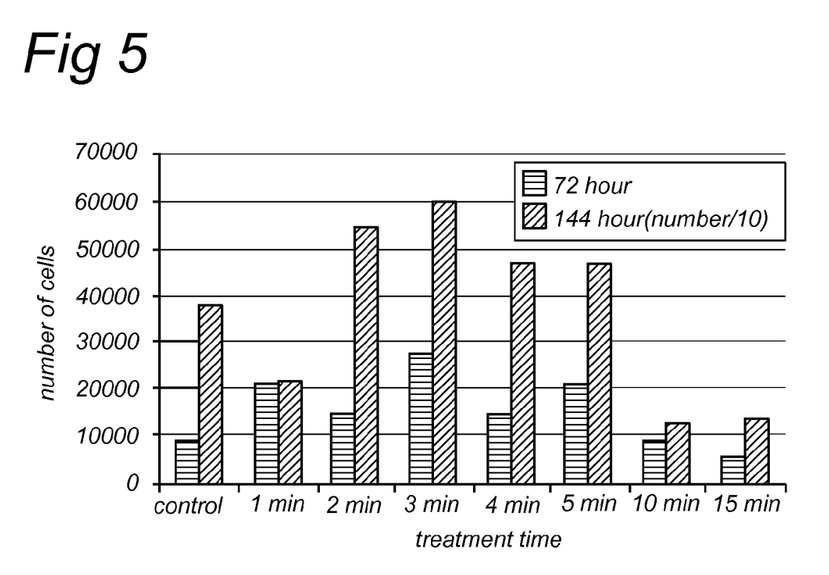

FIG. 4 is a graphical representation of the cell counts as function of the treatment time, the treatment time varying from 0 min (i.e. no treatment at all, in the control sample) and 15 minutes, for an incubation time of 0, 24 and 48 hours. FIG. 5 is a similar representation, illustrating cell counts after treatment times of 0-15 min and incubation time of 72-144 hours. The results show an increase in cell growth after 3 and 4 minutes of treatment time and a decrease in cell growth around 10 and 15 minutes of treatment time. Consequently, depending on the treatment time a noticeable effect on the cell growth was observed. For treatment times of about 2-5 minutes cell growth appeared to increases as compared to the control samples. For longer treatment times (i.e. treatment times of 10-15 minutes), the cell growth reduced, as compared to the control samples.

To test if the device could influence the growth rate of osteogenic cells we initiated testing the device on MC3T3-E1 cells.

MC3T3 E-1 cells were exposed for several minutes to an induced pulsed electromagnetic field, nanosecond pulse duration and frequency of 7 Hz. Different treatment times were chosen to look for optimal growth acceleration. After treatment they were plated at a density of 10.000 cells/cm$^2$ (n=3) and the growth rate of the cells was measured by cell count (n=3) and the metabolic activity was measured via Alamar Blue (n=3).

Figure 6:
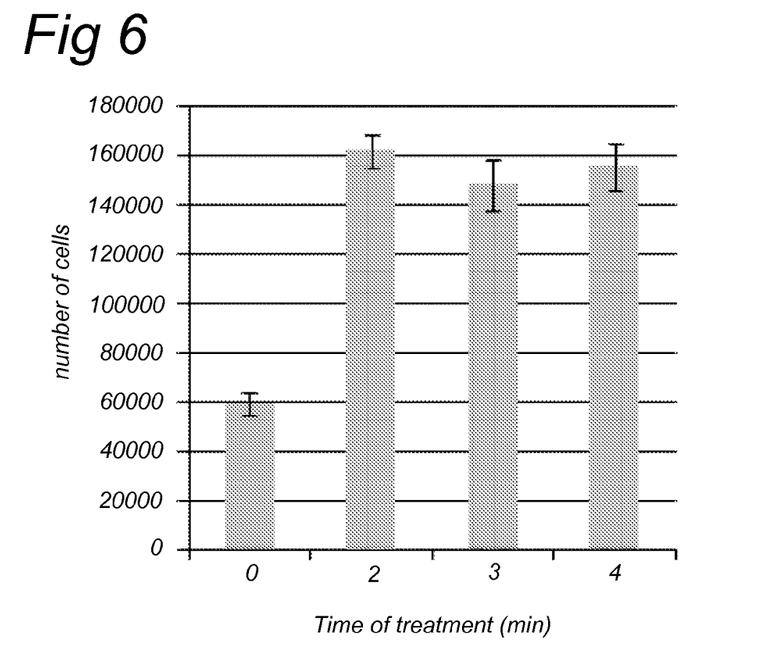
FIG. 6 is a graphical representation of the number of MC3T3 cells at day 3 after treatment.
Figure 7:
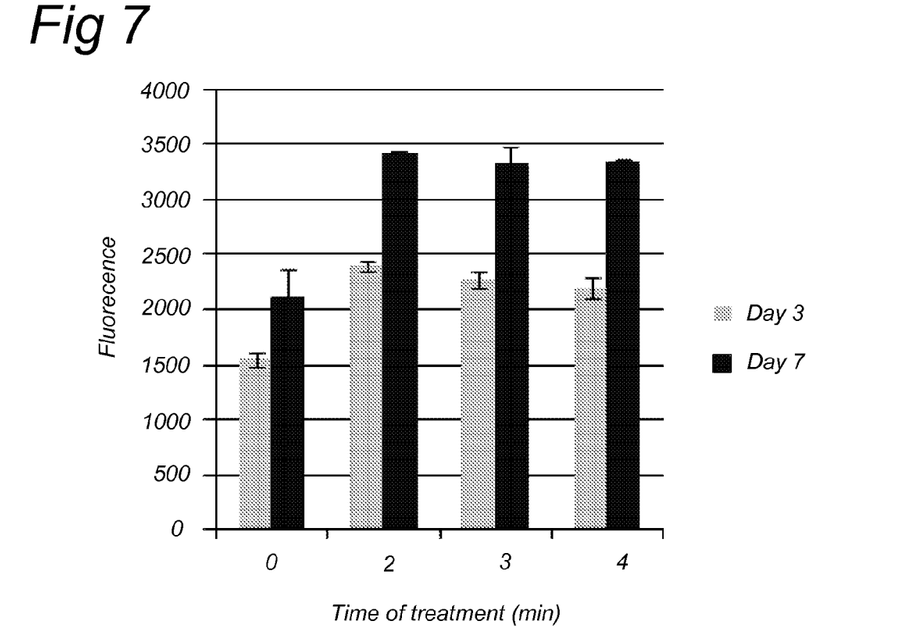
FIG. 7 is a graphical representation of the metabolic activity of MC3T3 cells at day 3 and 7 after treatment.

At day 3 the number of cells was counted and their metabolic activity was measured. As shown in FIG. 6, the cells submitted to treatment by the device grew significantly faster as compared to the control cells (0 min). These findings are supported by the data on the metabolic activity of the cells, as displayed in FIG. 7. Their activity is both after day 3 and 7 significantly increased in the treated cells. By microscopic observation the treated and control cells displayed a similar morphology (data not shown).

Two further cell-lines, HeLa cells and human keratinocytes, were investigated to see if they also displayed enhanced cell growth after being submitted to the electromagnetic field. Indeed it was found that also these cells showed an enhanced growth. The following table summarizes the results in terms of a growth ratio compared to control. A growth ratio >1 indicated increased growth whereas growth ratio <1 indicated decreased growth.

TABLE 1

| Enhanced cell growth | | |
|---|---|---|
| Cell-type | >1 growth ratio | <1 growth ratio |
| HeLa | 2-5 min. | 5+ min. |
| Keratinocytes | 3-6 min. | 6+ min. |
| 3T3 | 1.5-6 min. | 6+ min. |
| MC3T3-E1 | 2-5 min. | N/A |

The growth ratio is defined as the number of cells counted in the treated sample divided by the number of cells counted in the untreated sample (control group) several hours (e.g 24, 48, 72, 144) after exposure.

The metabolic activity (measured via Alamar Blue) of the keratonicytes was determined and also this showed an increase after being submitted to the electromagnetic field.

TABLE 2

| Enhanced metabolic activity | |
|---|---|
| Cell-type | >1 metabolic ratio |
| Keratinocytes | 3-4 min. |
| MC3T3-E1 | 2-4 min. |

The metabolic activity is defined as the metabolic activity of the cells in the treated sample divided by the metabolic activity of cells in the untreated sample (control group) at day 3 and day 7 after exposure.

In the context of the present invention, an increase in growth rate or an increase in metabolic activity means that the ratio of the treated cells compared to untreated cells is larger than 1. It is believed these effects can generally be found in all cell types, in particular mammalian cells types.

Clearly the increased cell growth and increased metabolic activity are advantageous in large scale production of cells per se and in particular in processes using cells for the production of biologically active compounds, e.g. proteins, antibodies, etc.

Thus the present invention also concerns a method of treating biological cells, the method comprising applying a pulsed electromagnetic field to the biological cells, the electromagnetic field having a field strength sufficiently high to affect the cell membranes and/or intracellular membranes of the biological cells, wherein the time duration of applying the field to the cells is kept between a minimum treatment time and a maximum treatment time, the treatment time being selected to increase the cell growth rate and/or the metabolic activity of the biological cells.

In one embodiment, the electric field to affect the biological cells is sufficiently high to increase the permeability of cell membranes and/or intracellular membranes of the biological cells.

In one embodiment, the field strength is generated by a current rise time of less than 10 ns, preferably less than 6 ns and the amplitude of the current pulse is at least 900 A, preferably about 1000 A.

In one embodiment, the electric field strength is between about 5-15 kV/cm, preferably between 8-12 kV/cm, more preferably about 10 kV/cm, and the minimum treatment time is preferably more than about 1 minute and preferably less than about 10 minutes.

Preferably the treatment time is from about 2 minutes to about 9, or about 8, or about 7, or about 6 minutes. Preferably the treatment time is from about 2 minutes to about 5 minutes.

Although the invention has been described with reference to specific embodiments thereof, it will be appreciated that invention is not limited to these embodiments and that changes and modifications to the system and method described herein may be made without departing from the invention. The rights applied for are defined by the following claims.

The invention claimed is:

1. A device for influencing the growth rate or metabolic activity of biological cells in an object, the device comprising:
   a single winding coil element being horseshoe-shaped;
   an electrical generator connected to the single winding coil element,
   the single winding being configured to be positioned essentially around the object, the object being inanimate; wherein
   the winding of the single winding coil element comprising two terminals defining a gap in between; and wherein
   the electrical generator being configured to discharge into the single winding coil element;
   the electrical generator comprising a power supply, a capacitor and a switching element, the switching element being configured for charging the capacitor in a first stage and discharging the capacitor in a second stage so as to provide a short duration high current into the single winding coil element, the short duration high current having a length of several hundreds of nanoseconds, the electrical generator being at least partly arranged in an enclosure and is pressurized to a predetermined high pressure value and the electrical generator being pressurized to a pressure of at least about 8 bar;
   the switching element being a serial two-gap spark gap switch configured to break down at a predefined discharge voltage; and
   an electric field having a field strength of between about 5-15 kV/cm generated by the single winding coil element comprising a superposition of rotational field and a conservative field so that the single winding coil element generates a short duration pulsed electromagnetic field by magnetic induction in the single winding coil element, the electromagnetic field having a field strength that is sufficiently high close to the gap in the single winding coil element to affect, preferably increase the permeability of, cell membranes and/or intracellular membranes of the biological cells contained in the object when in operation the object is placed inside the single winding coil element;
   the time duration of applying the pulsed field to the cells, the field strength and pulse frequency is selected to influence the growth rate or metabolic activity of the biological cells.

2. The device as claimed in claim 1, wherein the electromagnetic field is applied electrodelessly to the biological cells in the object.

3. The device as claimed in claim 1, wherein the single winding coil element is essentially cylindrical and defines a receiving space sized to allow the object comprising the biological cells to be removably placed.

4. The device as claimed in claim 1, wherein the single winding coil element defines a receiving space sized to allow the object to pass through the single winding.

5. The device as claimed in claim 1, wherein the single winding coil element is configured to allow placement of the object concentrically in the coil element.

6. The device as claimed in claim 1, wherein single winding coil is configured to affect the biological cells within the object without contact between the cells and the single winding coil.

7. The device as claimed in claim 1, wherein the electrical generator comprises a capacitor arranged so as to generate an electric field strength inside the single winding coil element of at least 10 kV/cm.

8. The device as claimed in claim 1, wherein the current rise time is 10 ns or less, the rate of change of the current (dI/dt) is at least 100 A/ns, the amplitude of the current pulse is about 500-2000 A, and/or the self-inductance of a circuit comprising the single winding coil element is several tens of nanoHenrys.

9. The device of claim 1, wherein the electromagnetic field has a field strength that is sufficiently high close to the gap in the single winding coil element to increase the permeability of cell membranes and/or intracellular membranes of the biological cells contained in the object.

10. The device as claimed in claim 8, wherein the current rise time is 6 ns or less and the rate of change of the current (dI/dt) is at least 150 A/ns.

11. The device as claimed in claim 1, wherein the cells are exposed to a short duration induced pulsed electromagnetic field, wherein the time duration of applying the pulsed field to the cells, the field strength and pulse frequency is kept between a minimum treatment time and a maximum treatment time, and wherein the pulse duration, frequency treatment time and field strength are selected to increase the cell growth rate of the biological cells or metabolic activity of the biological cells.

12. The device as claimed in claim 11, wherein the cells are exposed to a nanosecond pulse duration and frequency of at least 7 Hz, a time duration of the pulsed electromagnetic field of about 2-5 minutes, and an the electric field strength of at least 1 kv/cm.

13. The device as claimed in claim 12, wherein the electric field strength is 10 kv/cm.

14. An assembly comprising a device according to claim 1, and an object comprising a holder for holding a medium including the biological cells, the object being arranged in the single winding coil element.

15. The assembly according to claim 14, wherein the object is arranged in the single winding coil element.

16. The assembly according to claim 14, wherein the medium is a foodstuff.

17. The device as claimed in claim 1, wherein the object is a holder, a container, a carton or a package.

18. A device for influencing the growth rate or metabolic activity of biological cells in an object, the device comprising:
   a single winding coil element being horseshoe-shaped;
   an electrical generator connected to the single winding coil element,
   the single winding being configured to be positioned essentially around the object, the object being inanimate; wherein
   the winding of the single winding coil element comprising two terminals defining a gap in between;
   the electrical generator being configured to discharge into the single winding coil element; and wherein
   the electrical generator comprises a power supply, a capacitor and a switching element, the switching element being configured for charging the capacitor in a first stage and discharging the capacitor in a second stage so as to provide a short duration high current in the single winding coil element, the short duration high current having a length of several hundreds of nanoseconds, the generator being at least partly arranged in an enclosure and is pressurized to a predetermined high pressure value and the generator being pressurized to a pressure of at least about 8 bar; and wherein
   the switching element being a serial spark gap switch configured to break down at a predefined discharge voltage; and wherein
   an electric field generated by the single winding coil element comprising a superposition of rotational field and a conservative field so that the single winding coil element generates a short duration pulsed electromagnetic field by magnetic induction in the single winding coil element, the electromagnetic field having a field strength that is sufficiently high close to the gap in the single winding coil element to affect, preferably increase the permeability of, cell membranes and/or intracellular membranes of the biological cells contained in the object when in operation the object is placed inside the single winding coil element; and
   the time duration of applying the pulsed field to the cells, the field strength and pulse frequency being selected to influence the growth rate or metabolic activity of the biological cells.

19. The device as claimed in claim 18, wherein the object is a holder, a container, a carton or a package.

* * * * *